United States Patent [19]

Nakamatsu et al.

[11] Patent Number: 5,304,677
[45] Date of Patent: Apr. 19, 1994

[54] METHOD FOR PRODUCING 2,6-DIHYDROXYBENZOIC ACID

[75] Inventors: Toshio Nakamatsu; Yasuhiro Nishida, both of Hyogo; Norio Kometani, Osaka, all of Japan

[73] Assignees: Sumitomo Chemical Company, Limited; Sumika Fine Chemicals Co., Ltd., both of Osaka, Japan

[21] Appl. No.: 7,782

[22] Filed: Jan. 22, 1993

[30] Foreign Application Priority Data

Jan. 23, 1992 [JP] Japan ............................. 4-9906

[51] Int. Cl.$^5$ ............................................. C07C 65/01
[52] U.S. Cl. ........................................................ 562/476
[58] Field of Search .......................................... 562/476

[56] References Cited

FOREIGN PATENT DOCUMENTS 2000440 6/1987 Japan .
0215949 11/1968 U.S.S.R. .

*Primary Examiner*—Paul J. Killos
*Attorney, Agent, or Firm*—Sughrue, Mion, Zinn, Macpeak & Seas

[57] ABSTRACT

A method for producing 2,6-dihydroxybenzoic acid, which comprises heating an aqueous solution which contains a mixture of 2,6-dihydroxybenzoic acid and 2,4-dihydroxybenzoic acid and has a pH value of 4 or more, to selectively decompose 2,4-dihydroxybenzoic acid, and separating 2,6-dihydroxybenzoic acid from the decomposition reaction mixture.

7 Claims, No Drawings

METHOD FOR PRODUCING 2,6-DIHYDROXYBENZOIC ACID

FIELD OF THE INVENTION

The present invention relates to a method for producing 2,6-dihydroxybenzoic acid. More specifically, it relates to a method for producing 2,6-dihydroxybenzoic acid which comprises efficiently separating 2,6-dihydroxybenzoic acid from a mixture of 2,6-dihydroxybenzoic acid with 2,4-dihydroxybenzoic acid (the mixture being hereinafter referred to simply as "resorcylic acid mixture").

BACKGROUND OF THE INVENTION 2,6-Dihydroxybenzoic acid and 2,4-dihydroxybenzoic acid, which are usually obtained in the form of a resorcylic acid mixture via the carboxylation of resorcin, are separated from each other and then employed as starting materials for producing drugs, agricultural chemicals and industrial chemicals.

As an example of a method for separating these compounds, Chemical Abstracts, vol. 69, 67115j (1968) and ibid, vol. 71, 91014n (1969) report a method which comprises adding an acid to a resorcylic acid mixture in an alkaline solution so as to adjust the pH value to 2.6 to 2.7, then recovering 2,4-dihydroxybenzoic acid precipitated earlier, further adjusting the pH value to 1.0 to 1.5 and then recovering 2,6-dihydroxybenzoic acid precipitated later.

In recent years, 2,6-dihydroxybenzoic acid is increasing in the range of its use more than 2,4-dihydroxybenzoic acid and moreover required to have high purity.

In this respect, as an example of a method for separating 2,6-dihydroxybenzoic acid from a resorcylic acid mixture, JP-A-62-440 discloses, in Example 1 thereof, the following method: An acid is added to an alkaline aqueous solution of a resorcylic acid mixture containing 50% or more of 2,6-dihydroxybenzoic acid so as to adjust the pH value to 4. After removing the insoluble matters thus formed, the pH value of the solution is further adjusted to 1 and then the 2,6-dihydroxybenzoic acid thus precipitated is recovered. The term "JP-A" as used herein means an "published unexamined Japanese patent application".

In Example 1 of British Patent No. 916,548, an resorcylic acid mixture in an alkaline aqueous solution is acidified with hydrochloric acid and the 2,6-dihydroxybenzoic acid precipitated earlier is recovered. The 2,6-dihydroxybenzoic acid thus recovered is next dissolved again in water at 75° C. After removing insoluble matters, the solution is crystallized by cooling. Thus a purified product of 2,6-dihydroxybenzoic acid is obtained.

In Example 13 of the said British Patent, an alkaline aqueous solution of a resorcylic acid mixture is acidified and the precipitate thus formed is removed. Then seed crystals of 2,6-dihydroxybenzoic acid are added to the filtrate to deposit 2,6-dihydroxybenzoic acid, which is then separated.

In all the above-mentioned prior art methods, 2,6-dihydroxybenzoic acid is separated from 2,4-dihydroxybenzoic acid by controlling the pH value of an aqueous solution of a resorcylic acid mixture. In such methods, the resulting 2,6-dihydroxybenzoic acid is easy to be contaminated with 2,4-dihydroxybenzoic acid. Therefore, the 2,6-dihydroxybenzoic acid thus obtained has only a low purity and should be purified again.

SUMMARY OF THE INVENTION

An object of the present invention is to provide a method for industrially advantageously producing 2,6-dihydroxybenzoic acid by easily and efficiently separating 2,6-dihydroxybenzoic acid from a resorcylic acid mixture.

Other objects and effects of the present invention will be apparent from the following description.

The present inventors have conducted extensive studies to solve the above-mentioned problems in the prior art and attain the above objects. As a result, the present inventors have successfully found out that 2,4-dihydroxybenzoic acid can be selectively decomposed under specific conditions, thereby efficiently separating 2,6-dihydroxybenzoic acid of high purity.

The present invention relates to a method for producing 2,6-dihydroxybenzoic acid, which comprises heating an aqueous solution which contains a mixture of 2,6-dihydroxybenzoic acid and 2,4-dihydroxybenzoic acid and has a pH value of 4 or more, to selectively decompose 2,4-dihydroxybenzoic acid, and separating 2,6-dihydroxybenzoic acid from the decomposition reaction mixture.

DETAILED DESCRIPTION OF THE INVENTION

The resorcylic acid mixture used in the method according to the present invention can be prepared by carboxylation of resorcin. The carboxylation can be performed, for example, by the Kolbe-Schmitt reaction.

The Kolbe-Schmitt reaction of resorcin may be carried out by a known method. For example, resorcin is dissolved in a solvent and carbon dioxide gas is blown into the solution in the presence of a basic compound until the carbon dioxide gas is not absorbed any more. Thus a resorcylic acid mixture can be obtained.

Examples of the solvent used in the Kolbe-Schmitt reaction include water, organic solvents, e.g., alcohols, alkoxy-alcohols and dimethylformamide, and mixtures of these organic solvents and water. The solvent is generally used in an amount 2 to 10 times the weight of the resorcin.

Examples of the basic compound used in the Kolbe-Schmitt reaction include potassium carbonate, sodium carbonate, potassium hydroxide and sodium hydroxide. The basic compound is used approximately in an amount equimolar to resorcin.

The reaction may be carried out within a temperature range of from 100° to 200° C. under atmospheric pressure or a carbon dioxide gas pressure up to 30 kg/cm$^2$.

Although the content of 2,6-dihydroxybenzoic acid in the resorcylic acid mixture to be used in the present invention is not particularly restricted, it is preferably 10% by mol or more, and more preferably 30% by mol or more.

In the preparation of the resorcylic acid mixture-containing aqueous solution, the concentration of the resorcylic acid mixture preferably ranges from 5 to 30% by weight, although it is not particularly restricted.

When the resorcylic acid mixture is prepared by using an organic solvent, it is preferable to distill off the employed organic solvent. However, the resorcylic acid mixture-containing aqueous solution may contain a water-soluble organic solvent, so long as a temperature of the resorcylic acid mixture-containing aqueous solution can reach a desired level in the subsequent heating step of the present invention.

The pH value of the resorcylic acid mixture-containing aqueous solution is adjusted to 4 or more, preferably from 4 to 9, and more preferably from 5 to 7. The pH value may be adjusted by using an organic acid, e.g., acetic acid; a mineral acid, e.g., hydrochloric acid and sulfuric acid; or an alkali, e.g., an alkali hydroxide and an alkali carbonate. When the pH value is excessively low, the 2,6-dihydroxybenzoic acid is liable to decompose. When the pH value is excessively high, on the other hand, the decomposition rate of the 2,4-dihydroxybenzoic acid tends to be lowered.

The resorcylic acid mixture-containing aqueous solution having thus been adjusted to a desired pH value is then heated. The heating temperature is preferably 60° C. or more, and more preferably from 90° C. to the boiling temperature of the aqueous solution. The heating is generally continued until no undecomposed 2,4-dihydroxybenzoic acid is observed, and is usually completed within 1 to 5 hours. As the decomposition of the 2,4-dihydroxybenzoic acid proceeds, the pH value of the reaction system is increased. It is, therefore, preferable to carry out the heating treatment while controlling the pH value of the reaction mixture within the above-mentioned range by using the acid employed for adjusting the pH value of the aqueous solution.

Thus, the 2,4-dihydroxybenzoic acid in the resorcylic acid mixture can be selectively decomposed. The 2,6-dihydroxybenzoic acid of a high purity can be separated from the reaction mixture in a conventional manner such as, for example, acid-precipitation followed by filtration. The resorcin formed by the decomposition of the 2,4-dihydroxybenzoic acid may be recovered from the filtrate in a conventional manner and then reused.

According to the method of the present invention, 2,6-dihydroxybenzoic acid can be easily and efficiently separated on an industrial scale from a resorcylic acid mixture obtained by a known method and thus 2,6-dihydroxybenzoic acid of a high purity can be produced advantageously from an industrial viewpoint.

The present invention will be described in more detail by referring to the following examples. However, the present invention is not construed as being limited to these examples. In the following examples, all parts and percents are by weight.

EXAMPLE 1

50 Parts of resorcin was dissolved in 160 parts of ethanol, and 62.8 parts of anhydrous potassium carbonate was added thereto. After heating to 140° C., the mixture was kept at 140° C. for 4 hours under a carbon dioxide gas pressure of 14 kg/cm$^2$ while allowing to absorb 14 parts of carbon dioxide.

To the obtained reaction mixture containing 47 parts of a resorcylic acid mixture (63.1% of 2,6-dihydroxybenzoic acid and 36.9% of 2,4-dihydroxybenzoic acid), 300 parts of water was added and sulfuric acid was further added thereto until the pH value of the mixture reached 6. After distilling off 150 parts of a mixture of ethanol and water, the residue was refluxed at 98° to 100° C. for 3 hours to decompose the 2,4-dihydroxybenzoic acid. During the decomposition reaction, the pH value of the reaction mixture was controlled at 6 by appropriately adding sulfuric acid. The undecomposed 2,4-dihydroxybenzoic acid was monitored liquid-chromatographically and thus the end point of the decomposition was determined.

After completion of the decomposition reaction, sulfuric acid was added to the mixture until the pH value reached 3 and the insoluble matters thus formed were separated by filtration. Sulfuric acid was added to the filtrate until the pH value thereof reached 1. After cooling to 5° C., crystals of 2,6-dihydroxybenzoic acid thus formed were separated on a filter, washed with water and dried at 70° C. Thus 25 parts of a dry cake of 2,6-dihydroxybenzoic acid was obtained.

The result of the composition analysis on this product by liquid chromatography indicated that the purity of the 2,6-dihydroxybenzoic acid was 99.0%.

EXAMPLE 2

50 parts of resorcin was dissolved in 120 parts of ethanol and 150 parts of water, and 62.8 parts of anhydrous potassium carbonate was added thereto. After heating to 170° C., the mixture was kept at 170° C. for 5 hours under a carbon dioxide gas pressure of 18 kg/cm$^2$ while allowing to absorb 14 parts of carbon dioxide.

To the obtained reaction mixture containing 47.5 parts of a resorcylic acid mixture (56.8% of 2,6-dihydroxybenzoic acid and 43.2% of 2,4-dihydroxybenzoic acid), 150 parts of water was added and sulfuric acid was further added thereto until the pH value of the mixture reached 6. After distilling off 150 parts of a mixture of ethanol and water, the residue was refluxed at 98° to 100° C. for 3 hours to decompose the 2,4-dihydroxybenzoic acid. During the decomposition reaction, the pH value of the reaction mixture was controlled at 6 by appropriately adding sulfuric acid. The undecomposed 2,4-dihydroxybenzoic acid was monitored liquid-chromatographically and thus the end point of the decomposition was determined.

After completion of the decomposition reaction, sulfuric acid was added to the mixture until the pH value reached 3 and the insoluble matters thus formed were separated by filtration. Sulfuric acid was added to the filtrate until the pH value thereof reached 1. After cooling to 5° C., crystals of 2,6-dihydroxybenzoic acid thus formed were separated on a filter, washed with water and dried at 70° C. Thus 21 parts of a dry cake of 2,6-dihydroxybenzoic acid was obtained.

The result of the composition analysis on this product by liquid chromatography indicated that the purity of the 2,6-dihydroxybenzoic acid was 98.9%.

EXAMPLE 3

50 parts of resorcin was dissolved in 200 parts of water, and 62.8 parts of anhydrous potassium carbonate was added thereto. After heating to 180° C., the mixture was kept at 180° C. for 6 hours under a carbon dioxide gas pressure of 24 kg/cm$^2$ while allowing to absorb 14 parts of carbon dioxide.

To the obtained reaction mixture containing 46 parts of a resorcylic acid mixture (43.5% of 2,6-dihydroxybenzoic acid and 56.5% of 2,4-dihydroxybenzoic acid), sulfuric acid was added until the pH value of the mixture reached 5. The mixture was refluxed at 98° to 100° C. for 3 hours to decompose the 2,4-dihydroxybenzoic acid. During the decomposition reaction, the pH value of the reaction mixture was controlled at 6 by appropriately adding sulfuric acid. The undecomposed 2,4-dihydroxybenzoic acid was monitored liquid-chromatographically and thus the end point of the decomposition was determined.

After completion of the decomposition reaction, sulfuric acid was added to the mixture until the pH value reached 3 and the insoluble matters thus formed were separated by filtration. Sulfuric acid was added to the filtrate until the pH value thereof reached 1. After cooling to 5° C., crystals of 2,6-dihydroxybenzoic acid thus formed were separated on a filter, washed with water and dried at 70° C. Thus 13 parts of a dry cake of 2,6-dihydroxybenzoic acid was obtained.

The result of the composition analysis on this product by liquid chromatography indicated that the purity of the 2,6-dihydroxybenzoic acid was 98%.

While the invention has been described in detail and with reference to specific examples thereof, it will be apparent to one skilled in the art that various changes and modifications can be made therein without departing from the spirit and scope thereof.

What is claimed is:

1. A method for producing 2,6-dihydroxybenzoic acid, which comprises heating an aqueous solution which contains a mixture of 2,6-dihydroxybenzoic acid and 2,4-dihydroxybenzoic acid and has a pH value of 4 or more at a temperature of 60° C. or more, to selectively decompose 2,4-dihydroxybenzoic acid, and separating 2,6-dihydroxybenzoic acid from the decomposition reaction mixture.

2. A method as claimed in claim 1, wherein said mixture contains at least 10% by mol of 2,6-dihydroxybenzoic acid.

3. A method as claimed in claim 1, wherein said mixture is obtained by carboxylation of resorcin.

4. A method as claimed in claim 3, wherein said carboxylation is performed by the Kolbe-Schmitt reaction.

5. A method as claimed in claim 1, wherein the concentration of said mixture in said aqueous solution is from 5 to 30% by weight.

6. A method as claimed in claim 1, wherein heating is performed within a pH range of from 4 to 9.

7. A method as claimed in claim 1, wherein separating is performed by acid-precipitation.

* * * * *